United States Patent [19]

Tanaka et al.

[11] Patent Number: 5,494,824
[45] Date of Patent: *Feb. 27, 1996

[54] APPARATUS FOR MEASURING ALDEHYE

[75] Inventors: Toshiaki Tanaka, Numazu; Kiyokatsu Hibi; Toshihiko Miyaji, both of Tokyo, all of Japan

[73] Assignees: Nihon Bunko Kogyo Kabushiki Kaisha, Tokyo; Toyota Jidoshi Kabushiki Kaisha, Aichi, both of Japan

[*] Notice: The term of this patent shall not extend beyond the expiration date of Pat. No. 5,205,988.

[21] Appl. No.: 231,971

[22] Filed: Apr. 21, 1994

Related U.S. Application Data

[60] Continuation of Ser. No. 12,376, Feb. 2, 1993, abandoned, which is a division of Ser. No. 507,411, Apr. 5, 1990, Pat. No. 5,205,988.

[30] Foreign Application Priority Data

| Apr. 6, 1989 | [JP] | Japan | 1-87187 |
| Apr. 6, 1989 | [JP] | Japan | 1-87188 |
| Apr. 6, 1989 | [JP] | Japan | 1-87189 |

[51] Int. Cl.$^6$ .................... C12M 1/40
[52] U.S. Cl. .......... 435/288.7; 435/808; 435/287.9; 422/52; 422/81; 422/82.05; 422/82.08; 422/93
[58] Field of Search .............. 422/52, 62, 68.1, 422/81, 82, 82.05, 82.08, 91, 93, 100; 436/52, 53, 128, 130, 168, 172, 180; 435/26, 288, 807, 808

[56] References Cited

U.S. PATENT DOCUMENTS 3,681,025  8/1972  Dalgaard .................. 422/81 X (List continued on next page.)

FOREIGN PATENT DOCUMENTS 0296481  12/1988  Germany.

5052944  4/1980  Japan ...................... 435/190

OTHER PUBLICATIONS

Almuaibed, A. et al. "Determination of Acetaldehyde by Flow Injection Analysis with Soluble or Immobilized Aldehyde Dehydrogenase" Analytica Chimica Acta, vol. 198, (1987) pp. 37–44.

Ho, M. H. et al. "Enzymatic Methods for Determining Formaldehyde Release from Wood Products." Chemical Abstracts, vol. 105, No. 22 (Dec. 01, 1986), abstract 193184f.

Tanabe, K. et al. "Chemiluminescence Assay for NADH and its application to Determination of Biological Substances using 1–Methoxyphenazine Methosulfate and Isoluminol." Chemical Abstracts, vol. 106, No. 19 (May 11, 1987) abstract 152322b.

Potthast, K. et al. "Formaldehyde in Smokehouse Smoke and in Smoked Meat Products." Chemical Abstracts, vol. 106, No. 1 (Jan. 05, 1987) abstract 3929c.

Miksch, R. R. et al. "A Recommendation for Combining the Standard Analytical Methods for the Determinations of Formaldehyde and Total Aldehydes in Air." American Industrial Hygiene Association Journal, vol. 43, No. 5 (May 1982), pp. 362–365.

TerKonda, P. K. et al. "Monitoring Indoor Aldehydes." Chemical Abstracts, vol. 100, No. 24 (Jun. 11, 1984), abstract 197016x.

Bailey et al. (1986) "Biochemical Engineering Fundamentals", 2nd Ed., McGraw Hill, New York, pp. 666–696.

Primary Examiner—Jeffrey R. Snay
Attorney, Agent, or Firm—Browdy and Neimark

[57] ABSTRACT

Apparatus for measuring liquid aldehydes includes a liquid sample pouring mechanism for dividing a liquid sample which contains aldehydes into a formaldehyde measuring liquid sample and a total aldehyde measuring liquid sample and pouring the liquids separately from each other; a formaldehyde measuring mechanism for measuring the liquid formaldehyde in the formaldehyde measuring liquid sample; a total aldehyde measuring mechanism for measuring the liquid aldehydes in the total aldehyde measuring liquid sample; and a formaldehyde ratio calculating mechanism for calculating the ratio of the formaldehyde to the total aldehyde from the results of the measurements of the respective aldehyde measuring mechanisms.

3 Claims, 5 Drawing Sheets

U.S. PATENT DOCUMENTS

| | | | |
|---|---|---|---|
| 3,838,011 | 9/1974 | Hagen et al. | 436/52 |
| 3,840,341 | 10/1974 | Rogers | 436/146 |
| 3,941,659 | 3/1976 | Koch et al. | 435/26 |
| 3,948,731 | 4/1976 | Weaver | 435/29 |
| 4,519,983 | 5/1985 | Espitalie et al. | 422/93 X |
| 4,892,816 | 1/1990 | Akiba et al. | 435/11 |
| 4,960,711 | 10/1990 | Aoki et al. | 436/124 |
| 4,973,561 | 11/1990 | Hansen et al. | 436/52 |
| 5,152,963 | 10/1992 | Wreyford | 422/93 X |

APPARATUS FOR MEASURING ALDEHYE

This application is a continuation of application Ser. No. 08/012,376, filed Feb. 2, 1993, now abandoned, which is a division of Ser. No. 07/507,411, filed Apr. 5, 1990, now U.S. Pat. No. 5,205,988.

BACKGROUND OF THE INVENTION

1. Field of the Invention

The present invention relates to method and apparatus for measuring aldehydes and, more particularly, to the improvement of an aldehyde capturing mechanism and an aldehyde measuring mechanism.

2. Description of the Prior Art

Environmental disruption due to the increase in the aldehyde concentration and environmental disruption in rivers and lakes due to the aldehydes contained in factory wastes have recently become a social problem, and a great importance has been made on the analysis of the aldehydes in the automobile exhaust gas, factory wastes, etc.

In conventional methods adopted so as to measure aldehydes in a gas, aldehydes are monitored by an infrared spectrometer connected to a gas cell, or the aldehydes are measured by colorimetry by bubbling an aldehyde-containing gas to dissolve the aldehydes in the gas into water.

However, in the method of monitoring aldehyde by an infrared spectrometer connected to a gas cell, the infrared spectrometer has too low a sensitivity for the continuous monitoring of the gaseous aldehydes having a low concentration such as a of the order of ppb and requires a complicated operation.

The method of measuring the aldehydes by capturing them in an aqueous solution by bubbling has a problem in the responsiveness to a change in the aldehyde concentration in a gaseous sample, and it is difficult to change various capturing conditions, so that this method also has difficulty in the continuous monitoring of the aldehydes in a gas.

On the other hand, for measurement of liquid aldehydes, colorimetry was conventionally used, but in order to improve the sensitivity, the chemiluminescence quantitative analysis of formaldehde has recently been applied. For example, a chemiluminescence analysis using oxalic ester TCPO (bis (2,4,6-trichlorophenyl) oxalate) after converting formaldehyde into a fluorescent derivative by using Fluoral-P(4-amino-3-penten-2-one) has been developed.

A conventional chemiluminescence quantitative analysis, however, cannot be said to produce a sufficient sensitivity, and is also disadvantageous in that the measuring operation is so complicated that the responsiveness becomes too much deteriorated for the continuous monitoring of the solvent which has captured the aldehydes in a gas or factory wastes.

Thus, a measuring method which provides a higher sensitivity with a simple operation has been demanded.

SUMMARY OF THE INVENTION

Accordingly, it is an object of the present invention to eliminate the above-described problems in the prior art and to provide method and apparatus for measuring aldehydes which enables the secure capture of even an aldehyde having a low concentration and effective measurement thereof.

To achieve this aim, a continuous gaseous aldehyde measuring apparatus according to the present invention comprises a gaseous aldehyde capturing mechanism and an aldehyde measuring mechanism.

The gaseous aldehyde capturing mechanism captures the aldehyde in a gaseous sample into a continuously flowing capturing solvent.

The aldehyde measuring mechanism continuously measures the amount of aldehyde by reacting the aldehyde in the capturing solvent with a reagent in a flowing state.

A continuous gaseous aldehyde measuring apparatus according to the present invention preferably includes a compensating gas introducing portion and a standard liquid pouring portion.

The compensating gas introducing portion replaces a gaseous sample with a compensation gas which substantially contains no aldehyde and supplies the compensation gas to the gaseous aldehyde capturing mechanism.

The standard liquid pouring portion pours the standard aldehyde solution having a known concentration into the capturing solvent and supplies the capturing solvent to the aldehyde measuring mechanism.

In a continuous gaseous formaldehyde measuring apparatus, it is preferable that the aldehyde measuring mechanism selectively measures formaldehyde.

The aldehyde capturing mechanism according to the present invention includes a gaseous sample passage for passing the gaseous sample containing gaseous aldehydes therethrough, a capturing solvent passage for passing the capturing solvent which can dissolve the aldehydes therein and an aldehyde transmitting film portion which can transmit the aldehydes.

An aldehyde measuring method according to the present invention comprises an NADH producing step for reacting a liquid aldehyde with nicotinamide adenine dinucleotide (hereinunder referred to as "NAD") in the presence of an aldehyde dehydrogenase so as to produce reduced NAD (hereinunder referred to as "NADH") which corresponds to the amount of liquid aldehyde, and an NADH measuring step for measuring the amount of NADH produced.

The NADH measuring step preferably consists of a fluorescence measuring step for measuring the amount of NADH from the amount of fluorescence of the NADH.

It is preferable that the NADH measuring step preferably includes a luminescence reaction step for mixing a luminescent reagent for producing luminescence by the reaction with the NADH and an amount of luminescence measuring step for detecting the luminescence produced at the luminescence reaction step, and that the amount of liquid aldehyde is measured from the amount of NADH produced.

The aldehyde measuring method according to the present invention enables the measurement of only formaldehyde by using formaldehyde dehydrogenase which selectively oxidizes formaldehyde.

The aldehyde measuring apparatus according to the present invention comprises an NADH producing portion for reacting a liquid aldehyde with NAD in the presence of an aldehyde dehydrogenase so as to produce NADH which corresponds to the amount of liquid aldehyde, and an NADH measuring portion for measuring the amount of NADH produced.

The NADH measuring portion preferably consists of a fluorescence measuring portion for measuring the amount of NADH from the amount of fluorescence of the NADH.

The NADH measuring portion preferably includes a luminescence reaction portion for mixing a luminescent reagent for producing luminescence by the reaction with the NADH and an amount of luminescence measuring portion for detecting the luminescence produced by the luminescence reaction portion. The amount of liquid aldehyde is determined from the amount of NADH produced.

It is possible to measure only formaldehyde by using formaldehyde dehydrogenase which selectively oxidizes formaldehyde.

An aldehyde measuring apparatus according to the present invention comprises a liquid sample pouring mechanism for dividing the liquid sample which contains aldehydes into a formaldehyde measuring liquid sample and a total aldehyde measuring liquid sample and pouring them separately from each other, a formaldehyde measuring mechanism for measuring the liquid formaldehyde in the formaldehyde measuring liquid sample, a total aldehyde measuring mechanism for measuring the liquid aldehydes in the total aldehyde measuring liquid sample, and a formaldehyde ratio calculating mechanism for calculating the ratio of the formaldehyde to the total aldehyde from the results of the measurements of the respective aldehyde measuring mechanisms.

In the continuous gaseous aldehyde measuring apparatus according to the present invention, the aldehydes in the gaseous sample are first captured into the capturing solvent by the gaseous aldehyde capturing mechanism.

At this time, since the capturing solvent is continuously flowing, the change in the aldehyde concentration in the gaseous sample is accurately reflected in the change in the aldehyde concentration in the capturing solvent. Appropriate concentration is also possible by varying the capturing conditions as occasion demands.

Since the aldehyde measuring mechanism reacts the aldehyde in the capturing solvent with the reagent in a flowing state, it is possible to measure the change in the gaseous aldehyde concentration with good responsiveness and accuracy.

In this way, according to the continuous aldehyde measuring apparatus of the present invention, it is possible to measure the change in the gaseous aldehyde concentration with good responsiveness and accuracy.

In the continuous gaseous aldehyde measuring apparatus, which is provided with the compensating gas introducing portion and the standard liquid introducing portion, the aldehyde is removed from the capturing solvent by introducing a compensating gas from the compensating gas introducing portion in place of the gas sample.

By pouring a standard aldehyde liquid having a known concentration from the standard liquid pouring portion, it is possible to set the base and form an aldehyde calibration curve.

If the a measuring mechanism is as designed as to selectively measure formaldehyde, it is possible to measure the formaldehyde concentration, which particularly matters in the maintenance of the environment, with good responsiveness.

According to the method and apparatus for measuring aldehyde of the present invention, since liquid aldehydes are reacted with NAD in the presence of an aldehyde dehydrogenase, the amount of NADH produced is proportional to the amount of aldehyde present in the solution.

In addition, if NADH is measured by fluorimetry, it is measured with a much higher sensitivity as compared to conventional colorimetry.

If an aldehyde dehydrogenase is immobilized, it is possible to continuously measure the liquid sample in a flowing state with good responsiveness.

If the NADH produced in the above-described manner is measured by chemiluminescence analysis, a higher sensitivity is also obtained as compared to colorimetry.

If formaldehyde is selectively oxidized by formaldehyde dehydrogenase, NADH which corresponds to the amount of formaldehyde is produced, thereby enabling only the formaldehyde in the sample which contains various kinds of aldehydes to be measured with accuracy and a high sensitivity.

Furthermore, if the total aldehyde and formaldehyde are measured simultaneously and the ratio of the formaldehyde to the total aldehyde in the liquid sample is obtained, it is possible to obtain the ratio of generation of formaldehyde, which particularly matters in the maintenance of the environment, accurately and continuously.

The above and other objects, features and advantages of the present invention will become clear from the following description of the preferred embodiments thereof, taken in conjunction with the accompanying drawings.

DETAILED DESCRIPTION OF THE DRAWINGS

DESCRIPTION OF THE PREFERRED
EMBODIMENTS

Figure 1:
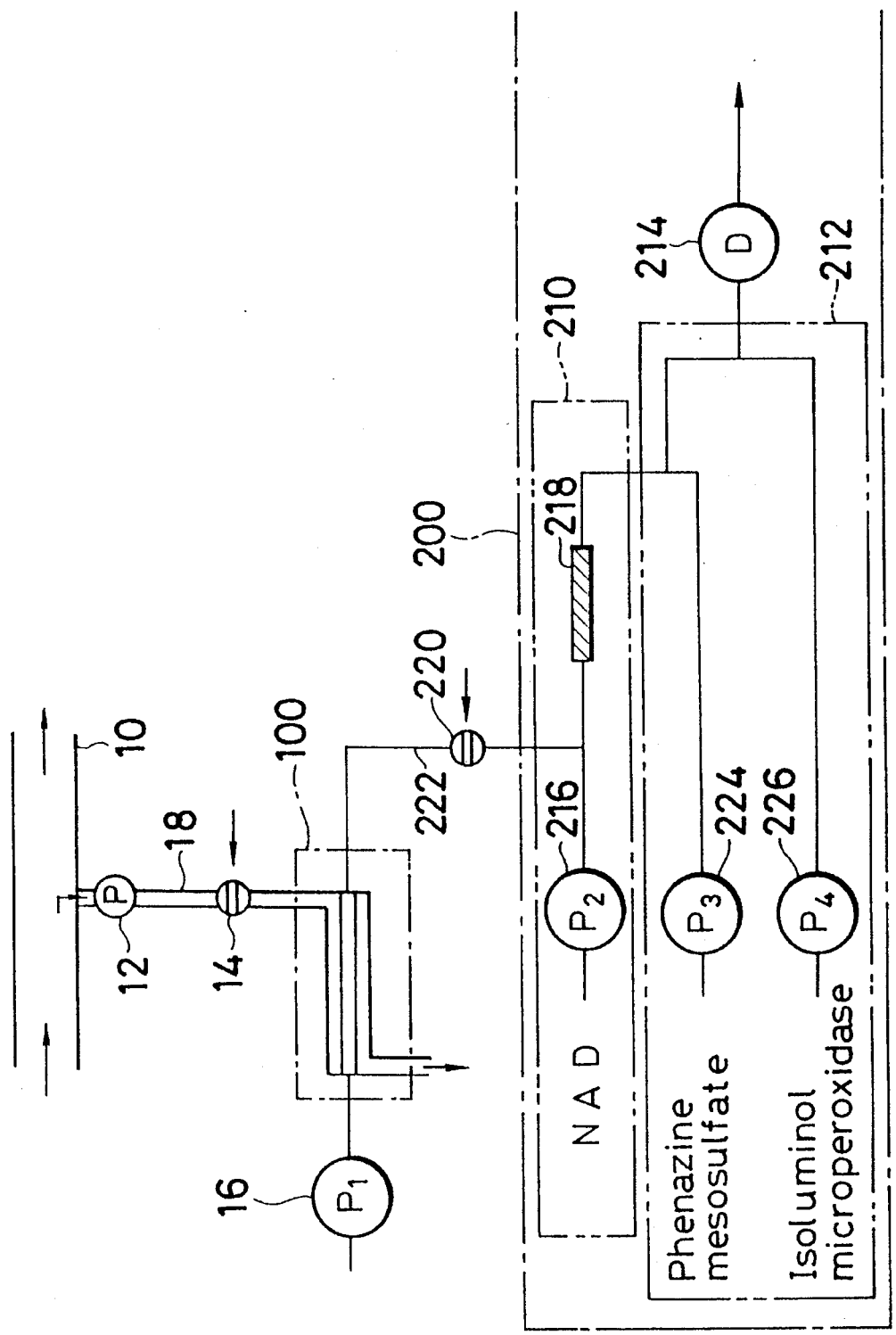
FIG. 1 is an explanatory view of a continuous gaseous aldehyde measuring apparatus according to an embodiment of the present invention.

FIG. 1 shows an embodiment of a continuous aldehyde measuring apparatus according to the present invention.

The continuous aldehyde measuring apparatus shown in FIG. 1 includes a gaseous aldehyde capturing mechanism 100 and an aldehyde measuring mechanism 200.

For example, a gaseous sample (exhaust gas) collected from the exhaust pipe 10 of an automobile is supplied to the gaseous aldehyde capturing mechanism through a pump 12 and a switching cock 14 (compensating gas introducing portion).

In the gaseous aldehyde capturing mechanism 100, a capturing solvent such as pure water which is supplied by the pump 16 captures the aldehydes in the exhaust gas, and the capturing solvent which has captured the aldehydes is supplied to the aldehyde measuring mechanism 200.

In the aldehyde measuring mechanism 200, the aldehyde concentration in the capturing solvent which has captured the aldehydes is measured in a flowing state, and the aldehyde concentration in the exhaust gas is calculated from the measured result and the amount of exhaust gas collected.

The aldehyde capturing mechanism 100 used in this embodiment will be explained in detail in the following.

Gaseous aldehyde capturing mechanism (gaseous aldehyde capturing device)

Figure 2:
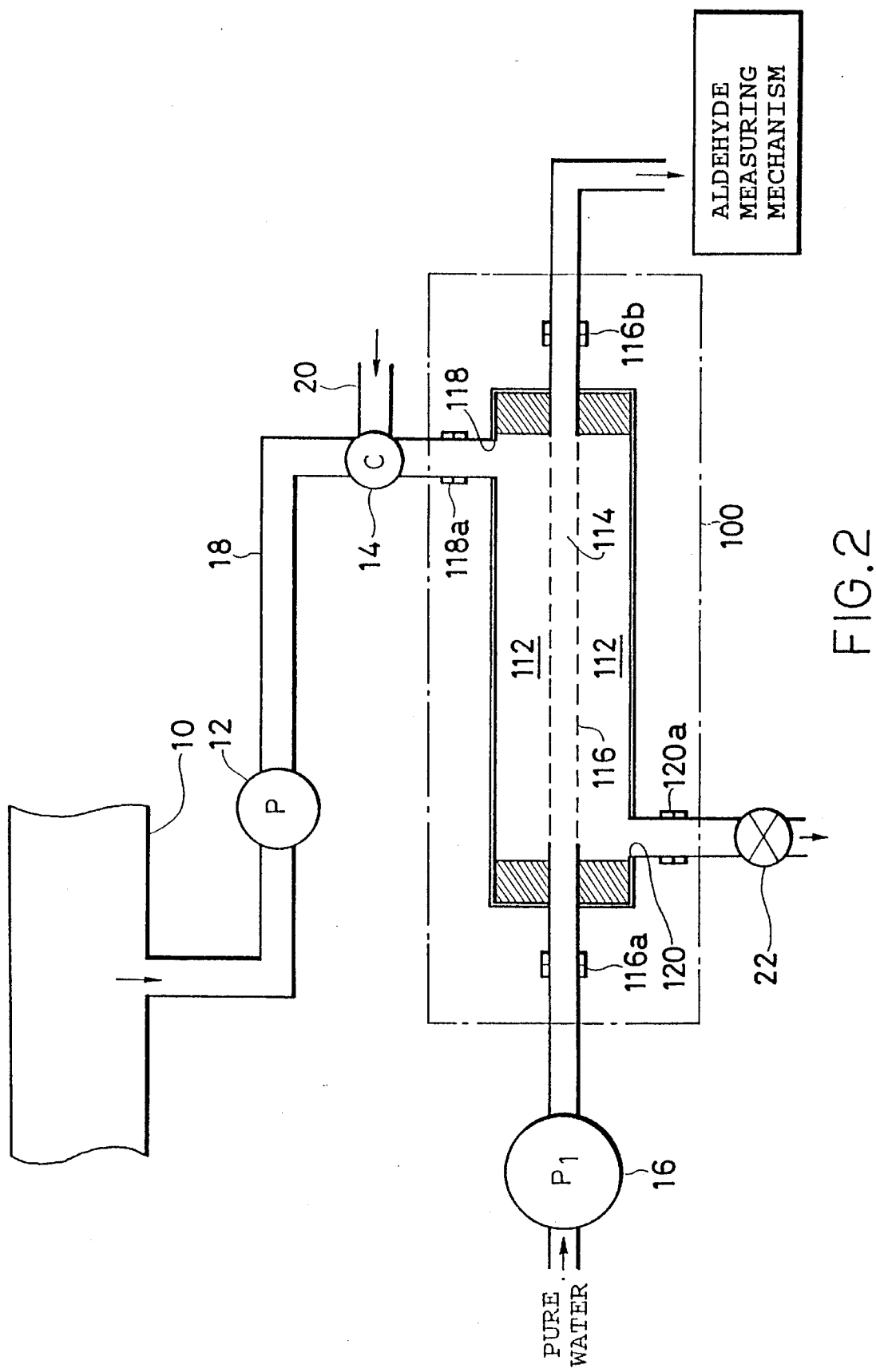
FIG. 2 is an explanatory view of the detailed structure of the gaseous aldehyde capturing mechanism used in the continuous gaseous aldehyde measuring apparatus shown in FIG. 1.

FIG. 2 shows the detailed structure of the gaseous aldehyde capturing mechanism 100 used in this embodiment.

In FIG. 2, the gaseous aldehyde capturing mechanism 100 includes a gaseous sample passage 112, a capturing solvent passage 114 and an aldehyde transmitting film portion 116.

The gaseous sample passage 112 is formed into a cylinder and a gaseous sample inlet 118 is provided at the left end portion while a gaseous sample discharge 120 is provided at the right end portion.

The aldehyde transmitting film portion 116 is formed from a pipe of a porous fluorine plastic film inserted into the gaseous sample passage 112, and the interior of which constitutes the capturing solvent passage 114 for passing the capturing solvent therethrough.

The left end portion of the aldehyde transmitting film portion 116 is connected to the pump 16 for supplying the capturing solvent (pure water, in this embodiment) and the right end portion thereof is connected to the aldehyde measuring mechanism 200.

The gaseous sample inlet 118 of the gaseous sample passage 112 is connected to, for example, the exhaust pipe 10 of an automobile through the switching cock 14 and the pump 12.

The switching cock 14 selectively switches between the gaseous sample passage 18 and a nitrogen gas (compensating gas) passage 20, and supplies a desired gas to the gaseous sample inlet 118.

The gaseous sample discharge 120 is connected to the gas discharge through a pressure valve 22.

The operation of the gaseous aldehyde capturing mechanism in this embodiment having the above-described structure will be explained hereinunder.

The pump 16 is first actuated so as to pass pure water through the capturing solvent passage 114 at a predetermined flow rate.

The switching cock 14 is then operated so as to connect the gaseous sample passage 18 to the gaseous sample inlet 118, and the pump 12 is actuated.

By these operations, the gaseous sample (exhaust gas) is collected through the exhaust pipe 10 at a predetermined flow rate and is introduced to the gaseous sample passage 112 through the switching cock 14.

The gaseous aldehydes in the gaseous sample transmit the aldehyde transmitting film portion 116 which consists of a porous fluorine plastic film. The gaseous aldehydes are then captured by the capturing solvent (pure water) which flows in the capturing solvent passage 114 and subsequently is supplied to the aldehyde measuring portion 200.

It is possible to control the aldehyde capturing ratio by varying the pressure in the gaseous sample passage 112 when the aldehydes in the gaseous sample pass therethrough.

It is also possible to place the aldehyde capturing mechanism 100 in a constant temperature module so as to heat the aldehyde capturing mechanism 100 to a predetermined temperature, if necessary.

More specifically, by heating the capturing mechanism 100, it is possible to accelerate the molecular motion of the sample component in the gaseous sample passage 112, to enhance the transmittance of the aldehyde film portion 116 and to reduce the the amount of foreign components which are not transmitted through the aldehyde transmitting film 118 and adsorbed by the film portion 116.

When the capturing operation of the aldehyde in the exhaust gas is completed, the switching cock 14 is operated so as to connect the nitrogen gas passage 18 to the gaseous sample inlet 118, and nitrogen gas as a compensating gas is introduced into the gaseous sample passage 112.

As a result, the exhaust gas in the gaseous sample passage 112 is subsequently discharged from the gaseous sample discharge 120 and the capturing solvent in the base state which contains no aldehyde is supplied to the aldehyde measuring mechanism 200.

In this way, it is possible to set the base and form the calibration curve simultaneously with the washing of each element of the capturing mechanism 100.

As described above, according to the gaseous aldehyde capturing mechanism 100 of this embodiment, it is possible to capture the aldehydes in the exhaust gas into the capturing solvent with good efficiency. In addition, since it is possible to adjust the flow rate of the capturing solvent in the capturing solvent passage 114 to a constant value, the responsiveness to a change in the aldehyde concentration of the gaseous sample is very good.

In addition, it is possible to adjust the temperature of the capturing mechanism 110, the flow rate of the capturing solvent, the flow rate of the gaseous sample, and the pressure of the gaseous sample by a simple operation so as to optimize these conditions in correspondence with the type of the gaseous sample and the measuring environment.

Although the tubular capturing solvent passage 112 is provided in the cylindrical gaseous sample passage 114 in this embodiment, it is also possible, for example, to provide the tubular gaseous sample passage 112 in the cylindrical capturing passage 114.

In this embodiment, it is also preferable to provide the bellows-like or spiral aldehyde transmitting film portion 116 in the gaseous sample passage 112 in order to increase the area of the aldehyde transmitting film portion as much as possible, thereby enhancing the aldehyde capturing efficiency.

In this embodiment, connectors 116a and 116b are replaceably provided at the connecting portion of the aldehyde transmitting film portion 116 and the pump 16 and at the connecting portion of the the aldehyde transmitting film portion 116 and the aldehyde measuring mechanism 200, respectively, connectors 118a and 120a are replaceably provided at the connection portion of the gaseous sample inlet 118 and the switching cock and at the connecting portion of the gaseous sample discharge 120 and the pressure valve 22, respectively. In this way, the aldehyde capturing mechanism 100 itself is made replaceable.

It is therefore possible to replace the capturing mechanism 100 as a whole when clogging is produced on the aldehyde transmitting film portion 116 or other portions are contaminated.

Aldehyde measuring mechanism (aldehyde measuring apparatus)

The aldehyde measuring mechanism 200 used in the continuous gaseous aldehyde measuring apparatus of this embodiment will now be explained with reference to FIG. 1.

The aldehyde measuring mechanism 200 in this embodiment includes an NADH producing portion 210, a luminescence reaction portion 212 and a chemiluminescence detector 214 which constitutes an amount of luminescence measuring portion.

The NADH producing portion 210 is composed of a pump 216 for supplying an NAD solution and an immobilized enzyme reactor 218. A liquid sample supply pipe 222 is connected to a portion between the pump 216 and the immobilized enzyme reactor 218 through a solution injector (standard liquid pouring portion) 220.

In the immobilized enzyme reactor 218, an aldehyde dehydrogenase is immobilized.

The luminescence reaction portion 212 uses phenazine mesosulfate, isoluminol and microperoxidase as a luminescent reagent which reacts with NADH.

The operation of the aldehyde measuring mechanism in this embodiment schematically having the above-described structure will now be explained.

The NAD solution supplied from the pump 216 and the sample solution supplied through the liquid sample supply pipe 222 are first introduced to the immobilized enzyme reactor 218 in a mixed state.

In the immobilized enzyme reactor 218, each aldehyde in the sample solution is oxidized the corresponding acid and NAD is reduced to NADH.

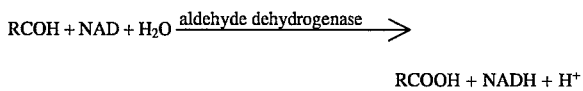

$$RCOOH + NADH + H^+$$

The phenazine mesosulfate solution is then supplied from a pump 224 and is mixed and reacts with the NADH-containing solution which is supplied from the NADH producing portion 210 to produce superoxide anion ($O_2^-$) or hydrogen peroxide ($H_2O_2$).

The isoluminol-microperoxidase mixed solution is supplied from a pump 226, and mixed with the reaction solution containing superoxide anion ($O_2^-$) or hydrogen peroxide.

As a result, a luminol reaction is brought about, and the amount of chemiluminescence is detected by the chemiluminescence detector 214.

The amount of luminescence detected by the chemiluminescence detector 214 in this way corresponds by mol to the amount of NADH produced, namely, the amount of aldehyde in the sample solution. By comparing the amount of luminescence with the amount of gaseous sample supplied by the pump 12, it is possible to measure the aldehyde concentration in the gaseous sample.

As described above, according to the continuous gaseous aldehyde measuring apparatus of this embodiment, since a luminol reaction is adopted, aldehyde measurement with a very high sensitivity is enabled.

It is possible to form an aldehyde calibration curve by pouring the aldehyde standard solution having a known concentration from the solution injector 220 and comparing the aldehyde concentration with the amount of luminescence detected by the chemiluminescence detector 214.

In the formation of the aldehyde calibration curve, it is necessary to switch the switching cock 14 to the side of the nitrogen gas passage 20 so as to prevent an aldehyde from being contained in the capturing solution which is flowing in the passage 222.

It is also preferable to introduce aldehyde standard gas having a known concentration in place of connecting the nitrogen gas passage 32 to the switching cock 24 so as to form a calibration curve with the capturing efficiency of the aldehyde capturing mechanism 100 taken into consideration.

In this way, it is possible to obtain the aldehyde concentration in the exhaust gas with accuracy.

It is also possible to use the aldehyde measuring mechanism in this embodiment as a liquid aldehyde measuring apparatus. In this case, it is possible to set the zero base and form a calibration curve by pouring the standard aldehyde solution from the solution injector 220 simultaneously with the supply of pure water from the pump 16 and comparing the aldehyde concentration with the result of the measurement by the chemiluminescence detector 214.

In this embodiment, an aldehyde dehydrogenase is immobilized in the immobilized enzyme reactor 218, but if immobilized formaldehyde dehydrogenase, for example, is used, only formaldehyde of all the aldehydes in the sample solution is oxidized to produce NADH, thereby enabling the measurement of the formaldehyde concentration in the sample solution.

Figure 3:
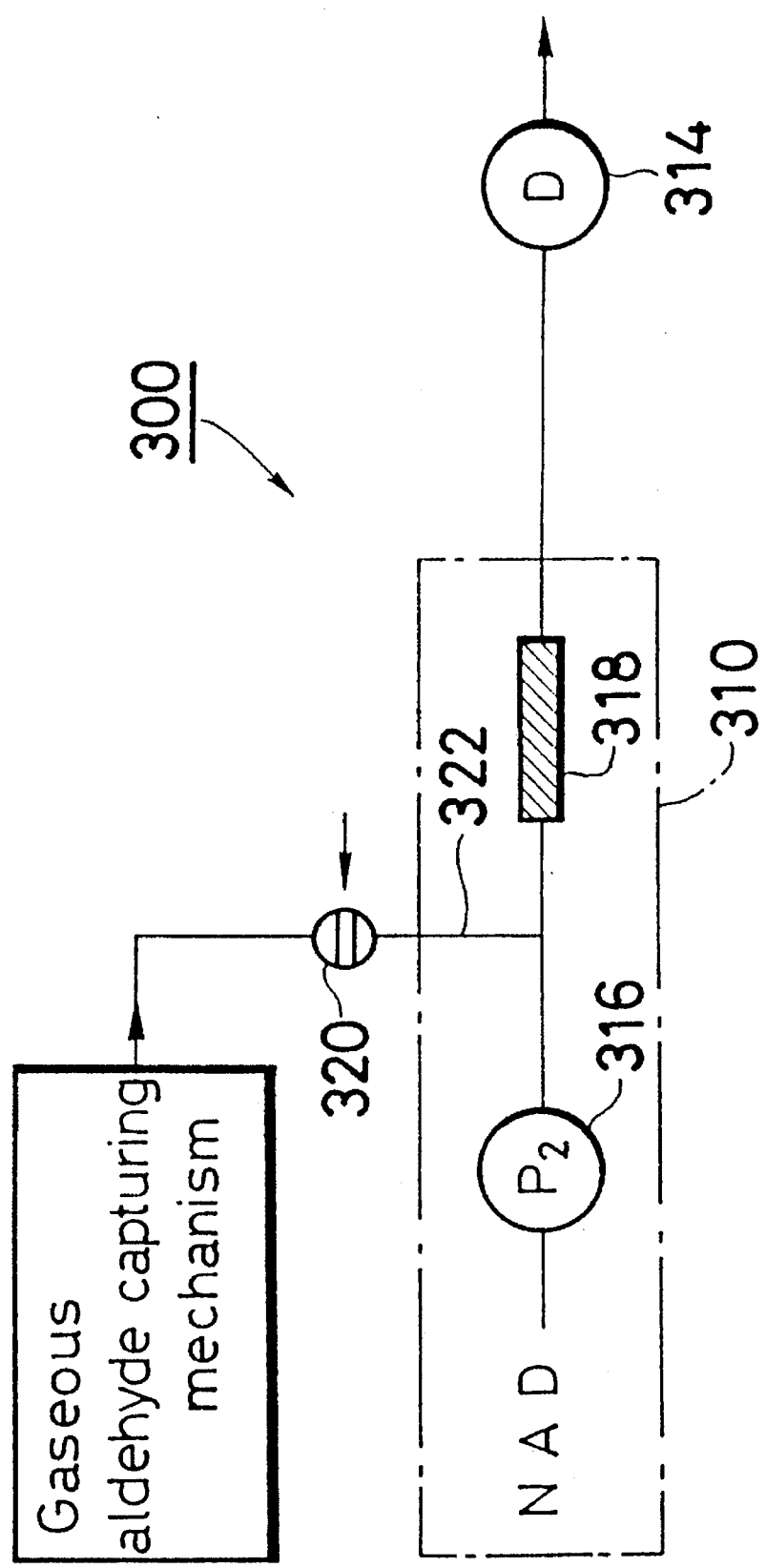
FIGS. 3 and 4 are explanatory views of other aldehyde measuring mechanisms.

FIG. 3 shows the structure of an aldehyde measuring mechanism according to a second embodiment of the present invention. The elements corresponding to those shown in FIG. 1 are indicated by the same numerals with 100 added thereto and explanation thereof will be omitted.

An aldehyde measuring mechanism 300 is composed of an NADH producing portion 310 and a fluorescence measuring instrument 314.

The NADH producing portion 310 produces NADH which corresponds to the amount of aldehyde existence in a gaseous sample in the same way as in the measuring mechanism shown in FIG. 1.

NADH is directly measured by the fluorescence measuring instrument 314. The measuring mechanism of this embodiment therefore enables the amount of aldehyde in a gaseous sample to be measured and obtained with simpler reaction and operation.

In the same way as in the apparatus shown in FIG. 1, it is possible to set the zero base and form a calibration curve by connecting the switching cock 14 to the nitrogen gas passage 20, pouring the standard aldehyde solution from a solution injector 320 and comparing the aldehyde concentration with the result of the measurement by the fluorescence measuring instrument 314.

In this embodiment, an aldehyde dehydrogenase is also immobilized in the immobilized enzyme reactor 218, but if immobilized formaldehyde, for example, is used, only formaldehyde of all the aldehydes in the sample solution is oxidized and produces NADH, thereby enabling the measurement of the formaldehyde concentration in the sample solution.

Figure 4:
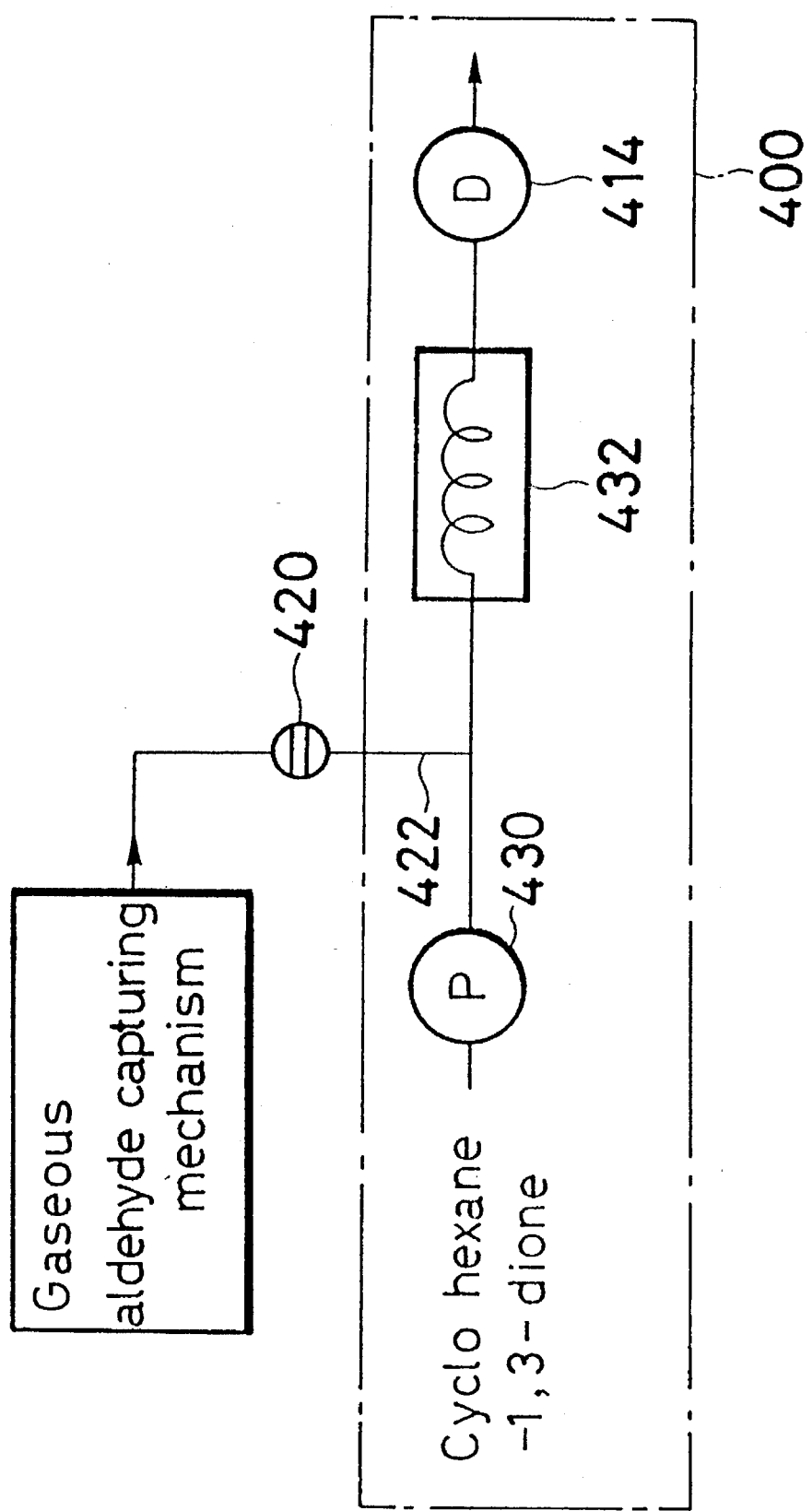

FIG. 4 shows the structure of an aldehyde measuring mechanism according to a third embodiment. The elements corresponding to those shown in FIG. 1 are indicated by the same numerals with 200 added thereto and explanation thereof will be omitted.

In this embodiment, cyclohexane-1, 3-dione is supplied by a pump 430 and mixed with the aldehyde capturing solvent. The resultant mixture is introduced to a heated reaction coil 432 and the reaction product of the aldehydes and cyclohexane-1, 3-dione is measured by a fluorescence detector 414.

As described above, according to the gaseous aldehyde capturing mechanisms 100 of these embodiments, it is possible to capture the aldehydes in a gaseous sample such as exhaust gas of an automobile efficiently and continuously.

If the gaseous aldehyde capturing mechanism 100 is used together with the aldehyde measuring mechanism 200 or 300, the liquid aldehyde which flows in the passage 222, 322 is reacted with NAD by a predetermined immobilized enzyme and the amount of NADH produced is measured by a chemiluminescence method or a fluorescence method, so that it is possible to measure a trace amount of aldehyde with accuracy. In addition, it is possible to select a desired object of measurement such as formaldehyde and the total aldehyde by varying the kind of the immobilized enzyme which constitutes the immobilized enzyme reactor 218, 318.

Furthermore, if the gaseous aldehyde capturing mechanism 100 is used together with the aldehyde measuring mechanism 400, total gaseous aldehyde can be measured easily.

As explained above, according to the continuous gaseous aldehyde measuring apparatuses of these embodiments, since the aldehydes in a gaseous sample are captured by the capturing solvent, it is possible to capture a trace amount of aldehyde efficiently, continuously and stably.

In addition, since the aldehyde concentration in the capturing solvent is measured in a flowing state, it is possible to measure the aldehyde concentration in the gaseous sample with good responsiveness and a high accuracy.

Figure 5:
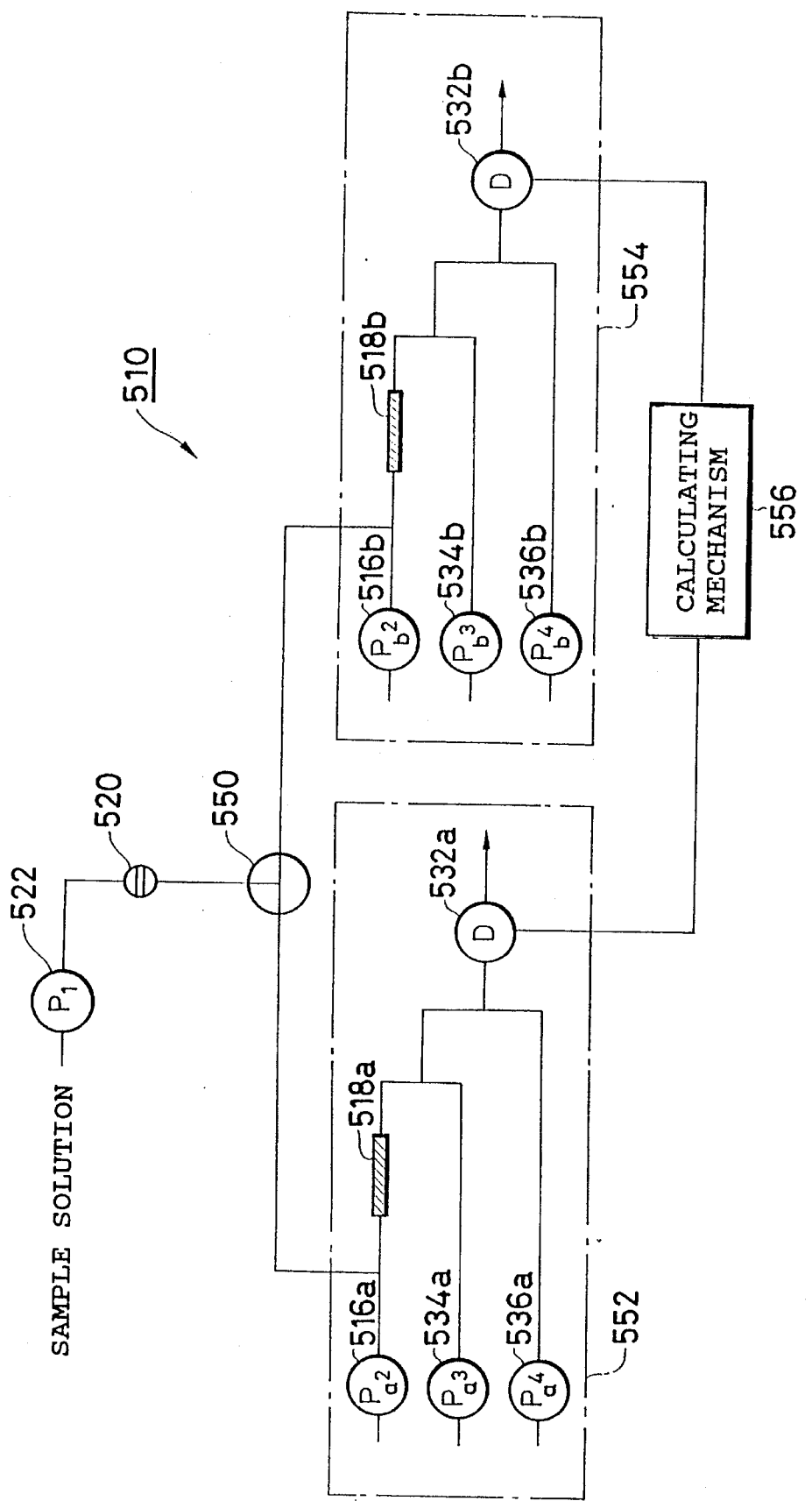
FIG. 5 is an explanatory view of a liquid aldehyde measuring apparatus according to another embodiment of the present invention.

FIG. 5 shows an aldehyde measuring apparatus according to a fourth embodiment of the present invention. The elements corresponding to those shown in FIG. 1 is indicated by the same numerals with 300 added thereto and explanation thereof will be omitted.

This embodiment is characterized in that the total aldehyde and formaldehyde are measured separately from each other, and the ratio of the formaldehyde to the total aldehyde is calculated.

For this purpose, the aldehyde measuring apparatus of this embodiment includes a division cock 550 which constitutes a sample pouring mechanism, a formaldehyde measuring mechanism 552, a total aldehyde measuring mechanism 554 and a formaldehyde ratio calculating mechanism 556.

The division cock 550 pours the sample liquid which contains aldehydes to the formaldehyde measuring mechanism 552 and the total aldehyde measuring mechanism 554.

The formaldehyde measuring mechanism 552 and the total aldehyde measuring mechanism 554 have substantially the same structure except that formaldehyde dehydrogenase is immobilized in the immobilized enzyme reactor 518a of the formaldehyde measuring mechanism 552 while an aldehyde dehydrogenase is immobilized in the immobilized enzyme reactor 518b of the total aldehyde measuring mechanism 554.

Therefore, the detection result corresponding only to the formaldehyde content is produced on the chemiluminescence detector 532a of the formaldehyde measuring mechanism 552 and the detection result corresponding to the total aldehyde content is produced on the chemiluminescence detector 532b of the total aldehyde measuring mechanism 554.

The results of measurements of the chemiluminescence detectors 532a and 532b of both mechanisms are input to the formaldehyde ratio calculating mechanism 556, wherein the ratio of the formaldehyde to the total aldehyde is calculated and the result is displayed on a display (not shown) or through a printer (not shown).

As described above, according to the liquid aldehyde measuring apparatus of this embodiment, since it is possible to measure the formaldehyde and the total aldehyde in the liquid with a high sensitivity, and simultaneously possible to measure and output the ratio of the formaldehyde to the total aldehyde, it is possible to continuously seize the state of existence of aldehyde in the liquid sample.

While there has been described what are at present considered to be preferred embodiments of the invention, it will be understood that various modifications may be made thereto, and it is intended that the appended claims cover all such modifications as fall within the true spirit and scope of the invention.

What is claimed is:

1. A continuous aldehyde measuring apparatus comprising:

a gaseous aldehyde capturing means comprising an aldehyde capturing solvent and a semipermeable membrane for continuously capturing aldehyde in a gaseous sample, whereby the gaseous sample is separated from the aldehyde capturing solvent by the semipermeable membrane;

a gaseous supply means for delivering a gaseous sample to said gaseous aldehyde capturing means;

a sample dividing means for continuously dividing the aldehyde capturing solvent into two samples, said two samples comprising a formaldehyde measuring sample and a total aldehyde measuring sample, and said sample dividing means pouring the formaldehyde measuring sample and the total aldehyde measuring sample separately from each other;

a formaldehyde measuring means for receiving and measuring the formaldehyde in said formaldehyde measuring sample in which liquid formaldehyde is reacted with NAD in the presence of formaldehyde dehydrogenase to produce NADH;

means for measuring total aldehyde comprising means for receiving and measuring the total aldehyde measuring sample wherein the total aldehyde measuring sample is reacted with NAD in the presence of aldehyde dehydrogenase immobilized in an enzyme reactor to produce NADH;

connector means between said gaseous aldehyde capturing means and the aldehyde measuring means whereby the gaseous aldehyde capturing means is readily separated from the aldehyde measuring means;

a gaseous sample discharge means for removing gaseous samples from said gaseous aldehyde capturing means;

a pressure valve provided at said gaseous sample discharge means to control aldehyde capturing ratio of said gaseous aldehyde capturing means by varying the gas pressure in said gaseous aldehyde capturing means;

compensating gaseous supply means for delivering gas free of aldehyde to said gaseous aldehyde capturing means;

a switching cock means in said gaseous supply means for alternatively supplying either gaseous sample or gas free of aldehyde to said gaseous aldehyde capturing means; and a formaldehyde ratio calculating means for calculating the ratio of said formaldehyde to the total aldehyde in the sample using the results of the measurements of the amount of NADH by the means for measuring total aldehyde and the formaldehyde measuring means.

2. A continuous aldehyde measuring apparatus according to claim 1 wherein said formaldehyde measuring means and total aldehyde measuring means comprise fluorescence measuring means for measuring the amount of NADH produced by measuring the amount of fluorescence of said NADH.

3. A continuous aldehyde measuring apparatus according to claim 1 wherein said formaldehyde measuring means and said total aldehyde measuring means comprise luminescent reaction means, means for mixing a luminescent reagent for producing luminescence by the reaction with NADH and means for detecting luminescence produced by said luminescence reaction means.

* * * * *

UNITED STATES PATENT AND TRADEMARK OFFICE
CERTIFICATE OF CORRECTION

PATENT NO. : 5,494,824
DATED : February 27, 1996
INVENTOR(S) : Toshiaki Tanaka, et al.

It is certified that error appears in the above-indentified patent and that said Letters Patent is hereby corrected as shown below:

On the title page, item [73] Assignee: Second named assignee, should read –Toyota Jidosha Kabushiki Kaisaha--.

Signed and Sealed this

Fourth Day of August, 1998

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,494,824
DATED : February 27, 1996
INVENTOR(S) : Toshiaki Tanaka, et al.

It is certified that error appears in the above-identified patent and that said Letters Patent is hereby corrected as shown below:

```
On the title page, item [73] Assignee:   The second assignee,
should read --Toyota Jidosha Kabushiki Kaisha--.
```

Signed and Sealed this

First Day of June, 1999

Attest:

Q. TODD DICKINSON

*Attesting Officer*  *Acting Commissioner of Patents and Trademarks*